United States Patent [19]

Desai

[11] 4,330,622

[45] May 18, 1982

[54] ELIMINATION OF NON-MICROBIAL TURBIDITY IN CULTURE MEDIA

[75] Inventor: Jay S. Desai, Little Ferry, N.J.

[73] Assignee: Becton Dickinson & Co., Paramus, N.J.

[21] Appl. No.: 75,158

[22] Filed: Sep. 12, 1979

[51] Int. Cl.³ ............................................ C12Q 1/04
[52] U.S. Cl. ...................................... 435/34; 435/253; 435/800
[58] Field of Search ................... 23/230 B; 252/408 R; 260/112 B; 435/29, 34, 35, 253, 808, 800

[56] References Cited

U.S. PATENT DOCUMENTS

| | | | |
|---|---|---|---|
| 2,486,216 | 10/1949 | Silvernail et al. | 435/253 |
| 2,728,725 | 12/1955 | Gloor | 210/54 |
| 3,671,399 | 6/1972 | Cekoric, Jr. et al. | 435/34 |
| 3,770,631 | 11/1973 | Fekete et al. | 260/112 B |
| 3,798,320 | 3/1974 | Weiss et al. | 435/253 |
| 3,843,453 | 10/1974 | Freake | 435/29 |
| 3,894,844 | 7/1975 | Pinto et al. | 23/230 B |
| 3,955,925 | 5/1976 | Proksch et al. | 260/112 B |
| 4,110,077 | 8/1978 | Klein et al. | 260/112 B |
| 4,184,848 | 1/1980 | Batz et al. | 435/10 |
| 4,218,537 | 8/1980 | Buissiere | 435/34 |
| 4,221,866 | 9/1980 | Cotter | 435/34 |
| 4,273,867 | 6/1981 | Lin et al. | 435/7 |

FOREIGN PATENT DOCUMENTS 1202438  10/1965  Fed. Rep. of Germany ... 260/112 B

*Primary Examiner*—Peter A. Hruskoci
*Attorney, Agent, or Firm*—Louis E. Marn; Elliot M. Olstein

[57] ABSTRACT

In the culturing of micro-organisms, non-microbial turbidity in the supernate is prevented by including an adsorbant for components which cause such non-microbial turbidity; e.g., lipoproteins and/or chylomicrons, with such adsorbant being soluble in the culture media. The adsorbant sediments such components, and is particularly effective in culture media which include an anticoagulant. Carboxy Methyl Cellulose is a particularly effective adsorbant.

27 Claims, No Drawings

ELIMINATION OF NON-MICROBIAL TURBIDITY IN CULTURE MEDIA

This invention relates to the culturing of micro-organisms, and more particularly to a new and improved process and culture media for culturing micro-organisms.

In diagnosing certain illnesses, it becomes important to determine the presence of micro-organisms in body fluids; for example, in blood, spinal fluid, etc. Applicant has found that many cases, the supernate includes non-microbial turbidity, which creates difficulty in reading the true growth of micro-organisms necessary for a rapid diagnosis. The non-microbial turbidity presents a particular problem in culture media which includes an anticoagulant, as described, for example, in U.S. Pat. No. 3,671,399, with such anticoagulant being included in the culture media in order to prevent trapping of bacteria in the interior of a clot which may be formed in the absence of such anticoagulant.

The present invention is directed to improving the culturing of micro-organisms in a culture medium, and is particularly directed to improving the culturing of micro-organisms in a culture media which contains polyanionic compounds as an anticoagulant.

In accordance with the present invention, applicant has found that in culturing a fluid derived from the body, such as blood, in a culture media, components derived from the body fluid are precipitated, and such precipitate imparts bacteria-like turbidity which often results in misinterpretation of bacterial growth. As a result, in accordance with the present invention, applicant provides for an improved culture media by including in the culture media an adsorbant for the components in the body fluid which may be precipitated during the culturing, with such adsorbant being initially soluble in the culture media. In accordance with the present invention, any components derived from the body fluid which precipitate during the culturing are adsorbed by the adsorbant and sedimented to provide a clear supernatant to facilitate examination of true turbidity as evidence of microbial growth. Applicant has found that although such adsorbants are initially soluble in the culture media, upon addition of a body fluid and precipitation of components from the body fluid, such adsorbants come out of solution, adsorb such precipitated components and form a sediment to thereby provide a clear supernate.

The components which are present in the body fluid, and which may be precipitated during the culturing, are generally lipoproteins and/or chylomicrons, and in accordance with the present invention, such lipoproteins and/or chylomicrons are sedimented by the adsorbant to provide a clear supernate and thereby eliminate non-microbial turbidity.

The present invention has particular applicability to culture medium which include an anticoagulant; in particular a polyanionic anticoagulant.

The soluble adsorbant which is employed in the culture medium is non-toxic with respect to the micro-organisms, and the particular adsorbant will vary depending upon the culture medium. As representative examples of such adsorbants, there may be mentioned: Carboxymethyl cellulose, hydroxyethyl cellulose, hydroxypropyl cellulose, methyl cellulose, acacia gum arabic or salts thereof and similar compounds. The preferred adsorbant is carboxymethyl cellulose or salts thereof.

The polyanionic compound which may be employed as an anticoagulant is non-toxic with respect to the micro-organisms. Such anticoagulants are generally known in the art, and as representative examples thereof, there may be mentioned: (1) a sulfated polysaccharide; in particular, sodium amylosulfate, (2) polyethylene sulfonic acid or salt thereof, (3) polyvinyl sulfuric acid or salt thereof, (4) polystyrene sulfonic adid or salt thereof, (5) sulfate esters of polyoxyethylene ethers of aliphatic alcohols having from 12 to 18 carbon atoms, (6) monothioglycerol, (7) sulfonated naphthalenes and salts thereof, and (8) a salt of polyanethol sulfonate. Such compounds may be used alone or in combination with each other. Such compounds are generally described in U.S. Pat. No. 3,671,399, which is hereby incorporated by reference.

The adsorbant is present in the culture medium in an amount effective for sedimenting any materials precipitated from the body fluid during culturing. In general, such adsorbants are present in an amount of from 0.1% to 1% and preferably in an amount of from 0.1% to 0.3%. Similarly, the polyanionic compound, when used, is present in an amount effective to prevent coagulation during culturing. In general, such anticoagulant is present in an amount of from 0.025% to about 0.1%, and preferably in an amount of 0.025% to 0.06%.

The culture medium employed in the present invention may be any one of the wide variety of culture medium which are available for culturing micro-organisms. Thus, for example, the culture medium may be a trypticase Soy broth, a Columbia broth, a supplemented peptone broth, thioglycollate, and the like.

The manner in which the polyanionic compound and adsorbant are employed in the culturing may vary. Thus, for example, either or both of such compounds may be added to the body fluid specimen or into the culture medium. In accordance with the preferred embodiment, however, the culture medium is provided with the adsorbant and the anticoagulant, when employed, whereby it is only necessary to add the specimen thereto.

The culture medium, which includes the soluble adsorbant, and which may further include an anticoagulant, is employed for testing for the presence of microorganisms in a body fluid, such as blood, spinal fluid, lymph fluid, and the like, by culturing procedures generally known in the art. Thus, as known in the art incubation is effected at an elevated temperature, for example, in the order of 35° to 37° C. for a period of time which may range from several hours to a few days, and preferably overnight. In general, such time periods are in the order of 18 to 24 hours. In accordance with the present invention, components of the body fluid; in particular, lipoproteins and/or chylomicrons, which may be precipitated during the culturing, are sedimented by the adsorbant present in the culture media to thereby eliminate non-microbial turbidity which could result in a misinterpretation of bacterial growth.

The invention will be further described with respect to the following Examples; however, the scope of the invention is not to be limited thereby:

EXAMPLE I

To 45.0 ml. of Trypticase Soy Broth (TSB), which includes sodium amylosulfate (SAS), as an anticoagulant, 5.0 ml. of sterilely drawn blood (with high triglycerides) was added. The medium with blood was incubated at 35° C. for 18 to 24 hours. At the end of incubation period, turbidity was detected in the supernate of the medium. On microscopic examination, no microorganisms were detected. On further study, it was found that this turbidity was due to beta lipoproteins. In order to eliminate this non-microbial turbidity, fresh Trypticase Soy Broth with SAS was prepared with 0.3 percent (0.3 g/100 ml.) concentration of Carboxy Methyl Cellulose, (CMC) Sodium, Salt. When blood was added to 45.0 ml. of sterile medium with CMC according to the procedure described earlier, no turbidity was observed in the supernate of the TSB medium with 0.3% CMC. However, a control bottle without CMC, demonstrated dense turbidity as observed in the earlier experiment.

EXAMPLE II

Similar observations were made when the test in Example I was repeated with SPS (Sodium Polyanethol Sulfonate) as anticoagulant in place of SAS.

On addition of 0.3% CMC, the non-microbial turbidity was eliminated from the supernate, thus facilitating the proper observation of blood culture medium for turbidity as evidence of growth.

EXAMPLE III

Trypticase Soy Broth (TSB) was prepared without addition of any coagulants. To the test medium, 0.3% CMC was added. The medium was distributed in 45.0 ml. volume to the bottle. A control bottle containing TSB without CMC was also filled in the same manner into the bottle. The media were autoclaved at 121° C. for 15 minutes.

To sterile 45.0 ml. of medium (with CMC), 5.0 ml. of blood from the same donor was added. 5.0 ml. of blood was also added to the control bottle containing 45.0 ml. of TSB without CMC.

The media were incubated at 35° C. for 18–24 hours. At the end of the incubation period, the bottles were examined for turbidity. The medium with CMC did not demonstrate any turbidity in the supernate, whereas, dense turbidity was observed in the TSB bottle without CMC.

EXAMPLE IV

To 45 ml. of sterile Trypticase Soy Broth (TSB) with 0.5% Sodium Amylo Sulfate (SAS), 5.0 ml. of blood, obtained from a donor with high cholesterol level, was added under sterile conditions. The bottle was properly vented to provide aerobic condition and incubated for 24 hours at 37° C.

At the end of the incubation period, the bottle was examined. Dense turbidity was detected without any microbial growth. The absence of growth was confirmed by gram staining of the turbid broth.

In order to eliminate this non-microbial visible turbidity from the supernate, 0.3 percent of Sodium Carboxy Methyl Cellulose (CMC) was added to the TSB with SAS medium. Five (5.0) ml. blood was added to the medium collected sterilely from the same donor with high cholesterol. At the end of incubation after 24 hours at 37° C., the bottle was examined. No turbidity was evident in the supernate of the medium. Erythrocytes and other cellular material along with lipoproteins in blood were sedimented into a smooth uniform layer.

The observation was also made in the TSB medium with Sodium Polyanethole Sulfonate (SPS). Addition of CMC solved the problem of non-microbial turbidity in this medium also. Other blood culture media tried with CMC were Thioglycollate, Supplemented Peptone Broth and Columbia Broth. Non-microbial turbidity was eliminated from these media with blood, by addition of 0.3% CMC.

The present invention is particularly advantageous in that it eliminates the problem of non-microbial turbidity in culture media when analyzing microbial growth in a body fluid; in particular, blood. Thus, such elimination of non-microbial turbidity facilitates the examination of true turbidity as evidence of microbial growth for rapid diagnosis of certain infectious processes, such as, bacteremia.

Numerous modifications and variations of the present invention are possible in light of the above teachings and, therefore, within the scope of the appended claims, the invention may be practised otherwise than as particularly described.

I claim:

1. In a composition containing a culture medium for culturing micro-organisms present in a body fluid and a polyanionic anticoagulant comprising at least one member selected from the group consisting of (1) a sulfated polysaccharide; (2) polyethylene sulfonic acid or salt thereof, (3) polyvinyl sulfuric acid or salt thereof, (4) polystyrene sulfonic acid or salt thereof, (5) sulfate esters of polyoxyethylene ethers of aliphatic alcohols having from 12 to 18 carbon atoms, (6) monothioglycerol, (7) sulfonated naphthalenes and salts thereof, and (8) a salt of polyanethol sulfonate, the improvement comprising:

an absorbant for at least one material selected from the group consisting of lipoproteins and chylomicrons dissolved in the culture medium for sedimenting said material which precipitates from a body fluid during culturing to prevent non-microbial turbidity in the culture medium.

2. The composition of claim 1 wherein the adsorbant is present in an amount of from 0.1% to 1%, by weight.

3. The composition of claim 2 wherein the adsorbant is at least one member selected from the group consisting of carboxymethyl cellulose, hydroxyethyl cellulose, hydroxypropyl cellulose, methyl cellulose and acacia gum arabic and salts thereof.

4. The composition of claim 2 wherein the adsorbant is carboxymethyl cellulose or salt thereof.

5. The composition of claim 2 wherein the anticoagulant is at least one member selected from the group consisting of sodium amylosulfate and sodium polyanethol sulfonate.

6. The composition of claim 5 wherein the adsorbant is carboxymethyl cellulose or salt thereof.

7. The composition of claim 6 wherein the adsorbent is present in an amount of from 0.1% to 0.3%, by weight.

8. The composition of claim 2 wherein the adsorbent is present in an amount of from 0.1% to 0.3%, by weight.

9. The composition of claim 8 wherein the adsorbent is at least one member selected from the group consisting of carboxymethyl cellulose, hydroxyethyl cellulose, hydroxypropyl cellulose, methyl cellulose and acacia gum arabic and salts thereof.

10. The composition of claim 9 wherein the adsorbent is carboxymethyl cellulose or salt thereof.

11. The composition of claim 1 wherein the culture medium is selected from the group consisting of Trypticase Soy Broth, Columbia Broth, a supplemented Peptone Broth and Thioglycollate.

12. The composition of claim 11 wherein the adsorbent is present in an amount of from 0.1% to 0.3%, by weight.

13. The composition of claim 12 wherein the adsorbent is at least one member selected from the group consisting of carboxymethyl cellulose, hydroxyethyl cellulose, hydroxypropyl cellulose, methyl cellulose and acacia gum arabic and salts thereof.

14. The composition of claim 13 wherein the adsorbent is carboxymethyl cellulose or salt thereof.

15. In a process for determining micro-organisms in a body fluid by culturing thereof in a culture medium containing a polyanionic anticoagulant comprising at least one member selected from the group consisting of (1) a sulfated polysaccharide; (2) polyethylene sulfonic acid or salt thereof, (3) polyvinyl sulfuric acid or salt thereof, (4) polystyrene sulfonic acid or salt thereof, (5) sulfate esters of polyoxyethylene ethers of aliphatic alcohols having from 12 to 18 carbon atoms, (6) monothioglycerol, (7) sulfonated naphthalenes and salts thereof, and (8) a salt of polyanethol sulfonate, the improvement comprising:

said culturing of the body fluid being effected in said culture medium which further has an adsorbent for at least one material selected from the group consisting of lipoproteins and chylomicrons dissolved therein for sedimenting said material which precipitates from the body fluid during culturing to prevent non-microbial turbidity in the culture medium.

16. The process of claim 15 wherein the adsorbant is present in an amount of from 0.1% to 1%, by weight.

17. The process of claim 16 wherein the adsorbant is at least one member selected from the group consisting of carboxymethyl cellulose, hydroxyethyl cellulose, hydroxypropyl cellulose, methyl cellulose and acacia gum arabic and salts thereof.

18. The process of claim 17 wherein the adsorbant is carboxymethyl cellulose or salt thereof.

19. The process of claim 18 wherein the body fluid is blood.

20. The process of claim 16 wherein the anticoagulant is at least one member selected from the group consisting of sodium amylosulfate and sodium polyanethol sulfonate.

21. The process of claim 20 wherein the adsorbant is carboxymethyl cellulose or salt thereof.

22. The process of claim 21 wherein the body fluid is blood.

23. The process of claim 21 wherein the adsorbent is present in an amount of from 0.1% to 0.3%, by weight.

24. The process of claim 15 wherein the culture medium is selected from the group consisting of Trypticase Soy Broth, Columbia Broth, a supplemented Peptone Broth and Thioglycollate.

25. The process of claim 24 wherein the adsorbent is present in an amount of from 0.1% to 0.3%, by weight.

26. The process of claim 25 wherein the adsorbent is at least one member selected from the group consisting of carboxymethyl cellulose, hydroxyethyl cellulose, hydroxypropyl cellulose, methyl cellulose and acacia gum arabic and salts thereof.

27. The process of claim 15 wherein the adsorbent is present in an amount of from 0.1% to 0.3%, by weight.

* * * * *